United States Patent [19]

Pfister

[11] 4,228,171
[45] Oct. 14, 1980

[54] ANTICHLORINERGIC BRONCHODILATORS

[75] Inventor: Jurg R. Pfister, Los Altos, Calif.
[73] Assignee: Syntex (U.S.A.) Inc., Palo Alto, Calif.
[21] Appl. No.: 17,302
[22] Filed: Mar. 5, 1979
[51] Int. Cl.$^2$ .................. C07D 207/12; A61K 31/40; A61K 31/44
[52] U.S. Cl. .......................... 424/263; 260/376.25; 260/376.35; 260/326.36; 260/326.47; 424/274; 546/281
[58] Field of Search ................. 260/326.47, 326.25, 260/326.36, 326.35; 546/281; 424/274, 263

[56] References Cited
U.S. PATENT DOCUMENTS

| | | | |
|---|---|---|---|
| 3,091,570 | 5/1963 | Biel | 260/326.47 |
| 3,094,463 | 6/1963 | Biel | 260/326.47 |
| 3,138,614 | 6/1964 | Arnsworth et al. | 260/376.35 |

FOREIGN PATENT DOCUMENTS

| | | | |
|---|---|---|---|
| 629039 | 10/1961 | Canada | 260/326.47 |
| 1136338 | 9/1962 | Fed. Rep. of Germany | 260/326.47 |

OTHER PUBLICATIONS

Kaguwata et al.; Chem. Abs., vol. 80:44017s (1974).
Kaguwata et al.; Chem. Abs., vol. 80:66588f (1974).
Takada et al.; Chem. Abs., vol. 80:66587e (1974).
Traversa et al.; Chem. Abs., vol. 85:116533k.

*Primary Examiner*—Mary C. Lee
*Attorney, Agent, or Firm*—Alan M. Krubiner; Tom M. Moran; Gerard A. Blaufarb

[57] ABSTRACT

Compounds of the formula

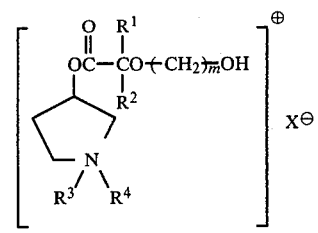

where $R^1$ and $R^2$ are the same or different and are phenyl optionally substituted with a substituent selected from the group $C_1$ and $C_6$ alkyl, $C_1$ and $C_6$ alkoxy and halo; or $C_4$ or $C_5$ heterocyclic aryl, the heteroatom selected from the group oxygen, nitrogen and sulfur; $R^3$ and $R^4$ are the same or different and are $C_1$ to $C_6$ alkyl; m is the integer 2 through 5; and X is selected from the group methanesulfonate, benzenesulfonate, p-toluene-sulfonate, nitrate, chloride, bromide and iodide. Methods for preparing these compounds are also disclosed. The compounds of the present invention are useful as anticholinergic agents.

5 Claims, No Drawings

ANTICHLORINERGIC BRONCHODILATORS

FIELD OF THE INVENTION

This invention relates to etherified glycolic acid esters and pharmaceutically acceptable, non-toxic salts thereof and to methods for preparing these compounds. More particularly this invention relates to pyrrolidinyl esters of etherified glycolic acids and to pharmaceutical compositions comprising one or more of the above compounds and to methods for achieving anticholinergic effects in mammals by using these compounds.

In summary, the compounds in accordance with the present invention can be represented by the following generic formula

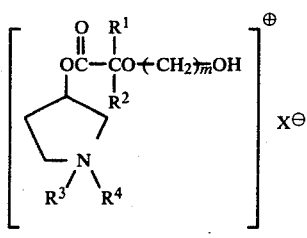

where $R^1$ and $R^2$ are the same or different and are phenyl optionally substituted with a substitutent selected from the group $C_1$ to $C_6$ alkyl, $C_1$ to $C_6$ alkoxy and halo; or $C_4$ or $C_5$ heterocyclic aryl, the heteroatom selected from the group oxygen, nitrogen and sulfur; $R^3$ and $R^4$ are the same or different and are $C_1$ to $C_6$ alkyl; m is the integer 2 through 5; and X is an anion which effectively forms a pharmaceutically acceptable, non-toxic salt and preferably is selected from the group methanesulfonate, benzenesulfonate, p-toluenesulfonate, nitrate, chloride, bromide and iodide.

The process for preparing the compounds of the present invention of Formula I comprises treating a compound of the formula

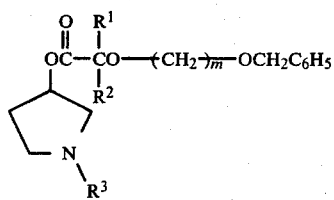

in which the hydroxy group is protected by a protecting group, with $R^4Z$, where $R^3$ and $R^4$ are defined above and Z is the group methanesulfonyl, benzenesulfonyl, p-toluenesulfonyl, chloro, bromo or iodo, and thereafter removing the protecting group.

The pharmaceutical compositions of the present invention include both solids or powders and solutions comprising one or more of the compounds of Formula I in combination with a suitable pharmaceutical solvent or dispersant, i.e., sterile water or pharmaceutical solid excipients.

The compounds, compositions and methods of the present invention herein before disclosed will become more readily apparent from the following description of preferred embodiments.

DESCRIPTION OF THE PREFERRED EMBODIMENTS

The compounds of the present invention are generically represented by Formula I below.

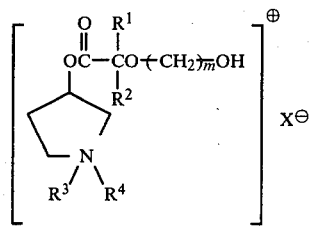

where $R^1$ and $R^2$ are the same or different and are phenyl optionally substituted with a substituent selected from the group $C_1$ to $C_6$ alkyl, $C_1$ to $C_6$ alkoxy and halo; or $C_4$ or $C_5$ heterocyclic aryl, the heteroatom selected from the group oxygen, nitrogen and sulfur; $R^3$ and $R^4$ are the same or different and are $C_1$ to $C_6$ alkyl; X is selected from the group methanesulfonate, benzenesulfonate, p-toluenesulfonate, chloride, bromide and iodide; and m is the integer 2 through 5.

In the compounds of the present invention of Formula I, $R^1$ and $R^2$ are the same or different and are preferably phenyl optionally substituted with a substituent selected from the group $C_1$ to $C_4$ alkyl, $C_1$ to $C_4$ alkoxy, chloro and bromo, or thienyl, m is the integer 2, 3 or 4, $R^3$ are the same or different and are $C_1$ $C_4$ alkyl and X is selected from the group methanesulfonate, benzenesulfonate, chloride and bromide.

Most preferred compounds of Formula I are those where $R^1$ and $R^2$ are the same or different and are methylphenyl, dimethylphenyl, phenyl or thienyl, $R^3$ and $R^4$ are the same or different and are methyl, ethyl, i-propyl or n-propyl, m is the integer 2 or 3 and X is chloride or bromide.

Particularly preferred compounds of Formula I are:
1,1-dimethyl-3-[2,2-diphenyl-2-(2-hydroxyethoxy)-acetoxy]pyrrolidinium bromide;
1,1-dimethyl-3-[2-phenyl-2-(thien-2-yl)-2-(2-hydroxyethoxy)acetoxy]pyrrolidinium chloride;
1,1-dimethyl-3-[2,2-dithien-2-yl-2-(2-hydroxyethoxy)acetoxy]pyrrolidinium iodide;

The compounds of the present invention of Formula I are made by the following process, depicted schematically:

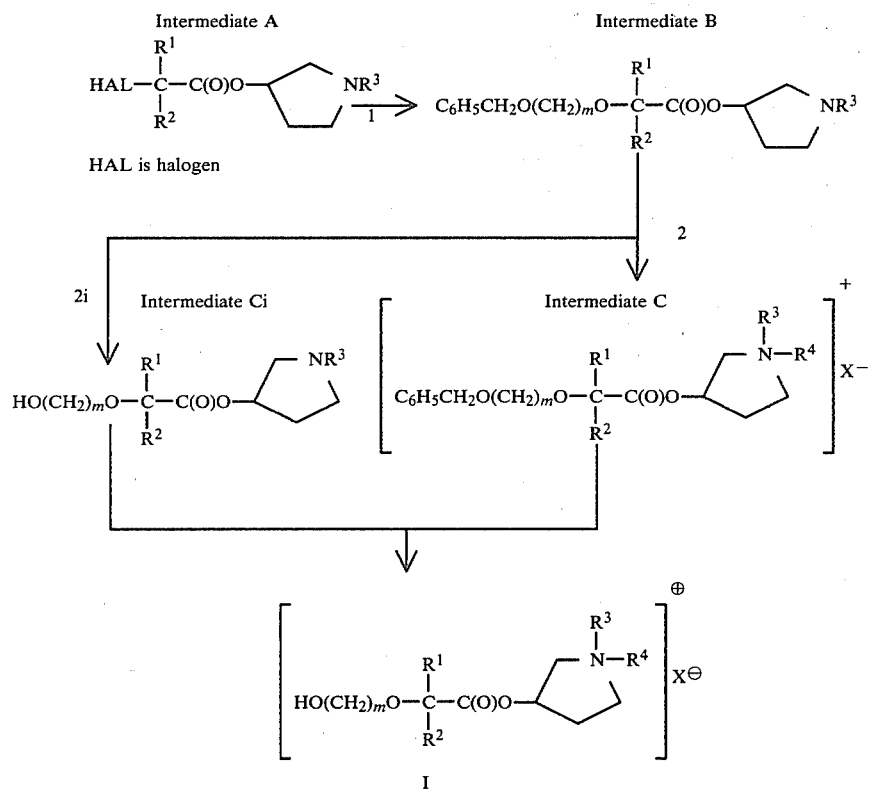

The initial reaction, shown in reaction step 1 involves the displacement of the group HAL on Intermediate A with the alkoxy moiety $C_6H_5CH_2O(CH_2)_mO-$ where m is the integer 2 through 5 to form Intermediate B. Typically the alkoxy moiety is in the form of the alcohol, i.e., $C_6H_5CH_2O(CH_2)_mOH$, such dissolved in a suitable, inert organic solvent such as ether, benzene, etc., optionally in the presence of a base such as pyridine, triethylamine, potassium carbonate, etc. and is treated with a solution of the pyrrolidine compound depicted above (Intermediate A) preferably at temperatures of from about 30° to about 150° for a time sufficient to complete the reaction, 30 minutes to 24 hours. While the alkoxy moiety as disclosed above bears a benzyl group, it should be understood that such group serves to protect the hydroxy function ultimately desired and shown in the compounds of Formula I. As such, any prior art group generally recognized by those skilled in the art as useful for protecting such hydroxy functionality can be employed in place of the benzyl group shown in the schematic diagram above. Such protecting groups include, for example, the groups diphenylmethyl, o-nitrobenzyl, p-nitrobenzyl, 3,5-dinitrobenzyl, p-methoxybenzyl, pivaloyloxymethyl, trichloromethoxycarbonyl, and the like.

This Intermediate (Intermediate B) is converted to Intermediate C (step 2), by reaction with a compound of the formula $R^4X$ where X is the group methanesulfonyl, benzenesulfonyl, p-toluenesulfonyl, chloro, bromo or iodo and $R^4$ is as previously defined. The reaction is typically carried out in an inert organic solvent, e.g., diethyl ether, methyl ethyl ketone, toluene, etc., at room temperature for a time sufficient to complete the reaction, typically 24 to 72 hours.

The glycolic acid ester, Intermediate C, preferably isolated from step 2 is subjected to hydrogenolysis to remove the protecting group at the ω-position of the alkoxy side chain (step 3). Preferably the reaction is conducted in acetic acid solution, in the presence of a hydrogenolysis catalyst for a time sufficient to assure completeness of the reaction. Various metal catalysts known in the art can be employed in this step such including platinum, Raney nickel, etc. Typically, the catalyst is palladium optionally on a substrate, e.g., carbon, aluminum oxide, barium sulfate, etc. The catalyst is most preferably palladium oxide or palladium black. The reaction is conducted at 20° to 60° and terminated when complete, i.e., after hydrogen uptake has ceased.

As an alternate method for the synthesis of the compounds of Formula I, Intermediate B may be subjected to the identical hydrogenolysis reaction as disclosed above for Intermediate C. This is shown in the reaction scheme as step 2i. The resulting compound, Intermediate Ci is then treated with a compound of the formula $R^4X$, where $R^4$ and X are as previously described, in a manner identical to the previously disclosed treatment of Intermediate B (step 3i).

The compounds of Intermediate A, essentially pyrrolidinyl esters of a disubstituted α-haloacetic acid, are readily prepared by any of the well known prior art esterification reactions. In the preferred embodiment, the above-disclosed pyrrolidinol is condensed with a 2-halo-2-$R^1$-2-$R^2$ acetyl chloride in the presence of a hydrogen chloride acceptor, such as pyridine, to provide Intermediate A. The reaction proceeds readily at room temperature in times of from about 5 minutes to about 24 hours. Solvents optionally used include any organic solvent inert to the reaction such as the aliphatic hydrocarbon solvents, e.g., hexane, heptane, octane, etc. or the aromatic hydrocarbon solvents, e.g. benzene, toluene, etc.

The compounds of the invention are predominantly antagonists of acetyl choline and are particularly effective as bronchodilators. As such, the compounds of this invention are typically administered in dosages of about from 0.01 to 5 mg per kg. of body weight. The precise effective dosage will, of course, vary depending upon the mode of administration, the condition being treated and the host. Where the compounds are used as pulmonary anticholinergics in mammals they are typically administered either orally, intravenously or by inhalation.

The compounds of the present invention can be administered in a wide variety of dosage forms, either alone or in combination with other pharmaceutically compatible medicaments, in the form of pharmaceutical compositions suited for oral, parenteral or aerosol administration. The compounds are typically administered as pharmaceutical compositions consisting essentially of the compounds of the invention and a pharmaceutical carrier. The pharmaceutical carriers can be either a solid material or a liquid in which the compound is dissolved, dispersed or suspended, and can optionally contain small amounts of preservatives and/or pH-buffering agents. Suitable preservatives which can be used include, for example, benzyl alcohol and the like. Suitable buffering agents include, for example, pharmaceutical phosphate salts and the like.

The liquid compositions can, for example, be in the form of solutions, emulsions, suspensions, syrups or elixirs and optionally can contain small quantities of preservatives and/or buffering agents, and preferably contain the therapeutic agents in convenient unit dosage.

The solid compositions can take the form of tablets, powders, capsules, pills and the like, preferably in unit dosage form for simple administration or precise dosages. Suitable solid carriers include, for example, pharmaceutical grades of starch, lactose, sodium saccharine, sodium bisulfite and the like.

Also based on studies on related compounds, it can be predicted that a number of the present compounds will exhibit useful anticholinergic activity when administered topically, intradermally or subcutaneously.

The compounds of Formula I can be administered as racemic mixtures or they can be administered as resolved enantiomers or optical isomers. In some instances, one enantiomer or optical isomer exhibits a greater anticholinergic effect than does the other corresponding enantiomer or optical isomer.

As used in the specification and the appended claims, the following terms have the meaning indicated. The term "halide" refers to fluoride, chloride, bromide and iodide. The term "heterocyclic aryl, the heteroatom selected from oxygen, nitrogen and sulfur" is intended to mean the monovalent heterocyclic radicals of aromatic character containing, in addition to the heteroatom, 4 or 5 carbon atoms in the ring. Examples of these radicals are pyrryl, for example 2- or 3-pyrryl, pyridyl, for example 2-, 3- or 4-pyridyl, thienyl, for example 2- or 3-thienyl and furyl, for example 2-furyl or 3-furyl. "Phenyl optionally substituted with a substituent selected from the group $C_1$ to $C_6$ alkyl, $C_1$ to $C_6$ alkoxy and halo" is intended to include unsubstituted phenyl, monosubstituted phenyl and polysubstituted phenyl. Such include methylphenyl, for example 2- or 3-methylphenyl, dimethylphenyl, for example 2,4- or 3,5-dimethylphenyl, methoxyphenyl, for example 2- or 3-methoxyphenyl, dimethoxyphenyl, for example 2,4- or 3,5-dimethoxyphenyl, halophenyl, for example 4-chlorophenyl, or 4-bromophenyl, or dihalophenyl, for example 2,4-dichlorophenyl or 2,4-dibromophenyl.

The compounds of Formula I may possess a chiral center. Accordingly, the compounds of the invention may be prepared in either their optically active form or as a racemic mixture. Unless otherwise specified, the compounds described herein are all in the racemic form. However, the scope of the subject invention is not to be considered limited to the racemic form, but to encompass the individual optical isomers of the compounds of the present invention.

Where desired the individual diastereomeric and optically isomeric compounds can be isolated by conventional separation and purification procedures in the case of diastereomers and by conventional resolution procedures in the case of optical isomers. Optimum physical, or physical-chemical, separation procedures and resolution procedures can be obtained by routine trial and error procedures well within the scope of those skilled in the art.

A further understanding of the invention can be had from the following non-limiting Preparations and Examples. As used hereinabove and below unless expressly stated to the contrary, all temperatures and temperature ranges refer to the Centigrade system and the terms ambient or room temperature refer to about 20° C. The term percent or (%) refers to weight percent and the term mole and moles refers to gram moles. The term equivalent refers to a quantity of reagent equal in moles to the moles of the preceding or succeeding reactant recited in that Preparation or Example in the terms of moles of finite weight or volume. As noted earlier, compounds having asymmetric centers and optical activity are isolated in their racemic form (±) unless otherwise indicated.

Preparation 1

A mixture of chlorodiphenylacetyl chloride (20 g), 1-methyl-3-pyrrolidinol (7.6 g), and pyridine (35 g) is kept at room temperature for two hours. After adding 45 g of 2-benzyloxyethanol, the mixture is refluxed gently for 18 hours. Excess pyridine and benzyloxyethanol are distilled off under reduced pressure, the residue is dissolved in ether and washed twice with water. The organic phase is dried over magnesium sulfate (MgSO$_4$), filtered and the filtrate evaporated to dryness. Chromatography of the residue on the silica gel with ethyl acetate-hexane-triethylamine (50:50:1) as eluent affords 18 g of 1-methyl-3-[2,2-diphenyl-2-(2-benzyloxyethoxy)acetoxy]pyrrolidine as an oil.

In a similar manner, the following compounds are prepared:
1-methyl-3-[2-(4-methylphenyl)-2-phenyl-2-(2-benzyloxyethoxy)acetoxy]pyrrolidine;
1-ethyl-3-[2-(4-methylphenyl)-2-phenyl-2-(2-benzyloxyethoxy)acetoxy]pyrrolidine;
1-methyl-3-[2-(thien-2-yl)-2-phenyl-2-(2-benzyloxyethoxy)acetoxy]pyrrolidine;
1-methyl-3-[2,2-dithien-2-yl-2-(2-benzyloxyethoxy)acetoxy]pyrrolidine;
1-methyl-3-[2-(pyrrol-2-yl)-2-phenyl-2-(2-benzyloxyethoxy)acetoxy]pyrrolidine;
1-methyl-3-[2,2-dipyrrol-2-yl-2-phenyl-2-(2-benzyloxyethoxy)acetoxy]pyrrolidine;

1-methyl-3-[2-(fur-2-yl)-2-phenyl-2-(2-benzyloxyethoxy)acetoxy]pyrrolidine;
1-methyl-3-[2,2-difur-2-yl-2-(2-benzyloxyethoxy)acetoxy]pyrrolidine.
1-methyl-3-[2-(4-methylphenyl)-2-phenyl-2-(3-benzyloxypropoxy)acetoxy]pyrrolidine;
1-ethyl-3-[2-(4-methylphenyl)-2-phenyl-2-(3-benzyloxypropoxy)acetoxy]pyrrolidine;
1-methyl-3-[2-(thien-2-yl)-2-phenyl-2-(3-benzyloxypropoxy)acetoxy]pyrrolidine;
1-methyl-3-[2,2-dithien-2-yl-2-(3-benzyloxypropoxy)acetoxy]pyrrolidine;
1-methyl-3-[2-(pyrrol-2-yl)-2-phenyl-2-(3-benzyloxypropoxy)acetoxy]pyrrolidine;
1-methyl-3-[2,2-dipyrrol-2-yl-2-phenyl-2-(3-benzyloxypropoxy)acetoxy]pyrrolidine;
1-methyl-3-[2-(fur-2-yl)-2-phenyl-2-(3-benzyloxypropoxy)acetoxy]pyrrolidine;
1-methyl-3-[2,2-difur-2-yl-2-(3-benzyloxypropoxy)acetoxy]pyrrolidine;
1-methyl-3-[2-(4-methylphenyl)-2-phenyl-2-(4-benzyloxybutoxy)acetoxy]pyrrolidine;
1-ethyl-3-[2-(4-methylphenyl)-2-phenyl-2-(4-benzyloxybutoxy)acetoxy]pyrrolidine;
1-methyl-3-[2-(thien-2-yl)-2-phenyl-2-(4-benzyloxybutoxy)acetoxy]pyrrolidine;
1-methyl-3-[2,2-dithien-2-yl-2-(4-benzyloxybutoxy)acetoxy]pyrrolidine;
1-methyl-3-[2-(pyrrol-2-yl)-2-phenyl-2-(4-benzyloxybutoxy)acetoxy]pyrrolidine;
1-methyl-3-[2,2-dipyrrol-2-yl-2-phenyl-2-(4-benzyloxybutoxy)acetoxy]pyrrolidine;
1-methyl-3-[2-(fur-2-yl)-2-phenyl-2-(4-benzyloxybutoxy)acetoxy]pyrrolidine; and
1-methyl-3-[2,2-difur-2-yl-2-(4-benzyloxybutoxy)acetoxy]pyrrolidine.

EXAMPLE 1

A solution of 12.4 g of the 1-alkylpyrrolidines of Preparation 1, and 11 g of methyl bromide in 180 ml methyl ethyl ketone is kept at 20° for 48 hours. The reaction mixture is evaporated to dryness to give 1,1-dimethyl-3-[2,2-diphenyl-2-(2-benzyloxyethoxy)acetoxy]pyrrolidinium bromide.

Similarly, the other 1-alkylpyrrolidines illustrated in Preparation 1 are alkylated to their respective pyrrolidinium salts.

EXAMPLE 2

In 60 ml of acetic acid is dissolved 1,1-dimethyl-3-[2,2-diphenyl-2-(2-benzyloxyethoxy)acetoxy]pyrrolidium bromide (1.5 g). The resulting solution is hydrogenated over 300 mg 10% Pd-C at 40° until the uptake of hydrogen ceases.

The filtered solution is evaporated to dryness, and the residue crystallized from methanol-ethyl acetate to give 1.06 g of 1,1-dimethyl-3-[2,2-diphenyl-2-(2-hydroxyethoxy)acetoxy]pyrrolidinium bromide, mp 213°–215°.

Similarly prepared are the following:
1,1-dimethyl-3-[2,2-diphenyl-2-(3-hydroxypropoxy)acetoxy]pyrrolidinium bromide (mp 128°–130°);
1,1-dimethyl-3-[2,2-diphenyl-2-(4-hydroxybutoxy)acetoxy]pyrrolidinium bromide (mp 153°–155°);
1,1-dimethyl-3-[2-(4-methylphenyl)-2-phenyl-2-(2-hydroxyethoxy)acetoxy]pyrrolidinium bromide;
1,1-dimethyl-3-[2-(thien-2-yl)-2-phenyl-2-(2-hydroxyethoxy)acetoxy]pyrrolidinium bromide;
1,1-dimethyl-3-[2,2-dithien-2-yl-2-(2-hydroxyethoxy)acetoxy]pyrrolidinium bromide;
1,1-dimethyl-3-[2-(pyrrol-2-yl)-2-phenyl-2-(2-hydroxyethoxy)acetoxy]pyrrolidinium bromide;
1,1-dimethyl-3-[2,2-dipyrrol-2-yl-2-phenyl-2-(2-hydroxyethoxy)acetoxy]pyrrolidinium bromide;
1,1-dimethyl-3-[2-(fur-2-yl)-2-phenyl-2-(2-hydroxyethoxy)acetoxy]pyrrolidinium bromide;
1,1-dimethyl-3-[2,2-difur-2-yl-2-(2-hydroxyethoxy)acetoxy]pyrrolidinium bromide.
1,1-dimethyl-3-[2-(4-methylphenyl)-2-phenyl-2-(3-hydroxypropoxy)acetoxy]pyrrolidinium bromide;
1-ethyl-3-[2-(4-methylphenyl)-2-phenyl-2-(3-hydroxypropoxy)acetoxy]pyrrolidinium bromide;
1,1-dimethyl-3-[2-(thien-2-yl)-2-phenyl-2-(3-hydroxypropoxy)acetoxy]pyrrolidinium bromide;
1,1-dimethyl-3-[2,2-dithien-2-yl-2-(3-hydroxypropoxy)acetoxy]pyrrolidinium bromide;
1,1-dimethyl-3-[2-(pyrrol-2-yl)-2-phenyl-2-(3-hydroxypropoxy)acetoxy]pyrrolidinium bromide;
1,1-dimethyl-3-[2,2-dipyrrol-2-yl-2-phenyl-2-(3-hydroxypropoxy)acetoxy]pyrrolidinium bromide;
1,1-dimethyl-3-[2-(fur-2-yl)-2-phenyl-2-(3-hydroxypropoxy)acetoxy]pyrrolidinium bromide;
1,1-dimethyl-3-[2,2-difur-2-yl-2-(3-hydroxypropoxy)acetoxy]pyrrolidinium bromide;
1,1-dimethyl-3-[2-(4-methylphenyl)-2-phenyl-2-(4-hydroxybutoxy)acetoxy]pyrrolidinium bromide;
1,1-dimethyl-3-[2-(4-methylphenyl)-2-phenyl-2-(4-hydroxybutoxy)acetoxy]pyrrolidinium bromide;
1,1-dimethyl-3-[2-(thien-2-yl)-2-phenyl-2-(4-hydroxybutoxy)acetoxy]pyrrolidinium bromide;
1,1-dimethyl-3-[2,2-dithien-2-yl-2-(4-hydroxybutoxy)acetoxy]pyrrolidinium bromide;
1,1-dimethyl-3-[2-(pyrrol-2-yl)-2-phenyl-2-(4-hydroxybutoxy)acetoxy]pyrrolidinium bromide;
1,1-dimethyl-3-[2,2-dipyrrol-2-yl-2-phenyl-2-(4-hydroxybutoxy)acetoxy]pyrrolidinium bromide;
1,1-dimethyl-3-[2-(fur-2-yl)-2-phenyl-2-(4-hydroxybutoxy)acetoxy]-pyrrolidinium bromide; and
1,1-dimethyl-3-[2,2-difur-2-yl-2-(4-hydroxybutoxy)acetoxy]pyrrolidinium bromide.

While the present invention has been described with reference to specific embodiments thereof, it should be understood by those skilled in the art that various changes may be made and equivalents may be substituted without departing from the true spirit and scope of the invention. In addition, many modifications can be made to adapt a particular situation, material or composition of matter, process, process step or steps or objective to the spirit of this invention without departing from its essential teachings.

I claim:

1. Compounds of the formula

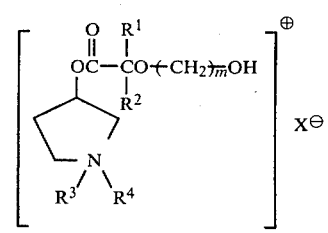

wherein $R^1$ and $R^2$ are the same or different and are phenyl optionally substituted with a substituent selected from the group $C_1$ to $C_6$ alkyl, $C_1$ to $C_6$ alkoxy and halo; or monovalent heterocyclic radical of aromatic character containing, in addition to a heteroatom which is oxygen, nitrogen or sulfur, 4 or 5 carbon atoms in the ring; $R^3$ and $R^4$ are the same or different and are $C_1$ to $C_6$ alkyl; m is the integer 2 through 5; and X is an anion which effectively forms a pharmaceutically acceptable, non-toxic salt.

2. The compounds in accordance with claim 1 wherein $R^1$ and $R^2$ are the same or different and are phenyl optionally substituted with a substituent selected from the group $C_1$ to $C_4$ alkyl, $C_1$ to $C_4$ alkoxy, chloro and bromo, or thienyl; $R^3$ and $R^4$ are the same or different and are $C_1$ to $C_4$ alkyl; m is the integer 2, 3 or 4; and X is selected from the group methanesulfonate, benzenesulfonate, chloride and bromide.

3. The compounds in accordance with claim 2 wherein $R^1$ and $R^2$ are the same or different and are phenyl, methylphenyl, dimethylphenyl or thienyl; $R^3$ and $R^4$ are the same or different and are methyl, ethyl, i-propyl or t-butyl; m is the integer 2 or 3; and X is chloride or bromide.

4. An anticholinergic composition which comprises a suitable pharmaceutical solvent or dispersant and at least one compound of the formula

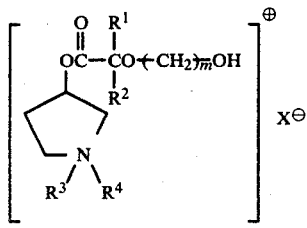
(I)

wherein $R^1$ and $R^2$ are the same or different and are phenyl optionally substituted with a substituent selected from the group $C_1$ to $C_6$ alkyl, $C_1$ to $C_6$ alkoxy and halo; or; monovalent heterocyclic radical of aromatic character containing, in addition to a heteroatom which is oxygen, nitrogen or sulfur, 4 or 5 carbon atoms in the ring; $R^3$ and $R^4$ are the same or different and are $C_1$ to $C_6$ alkyl; m is the integer 2 through 5; and X is an anion which effectively forms a pharmaceutically acceptable, non-toxic salt.

5. A method for effecting bronchodilation in mammals which comprises administering to said mammals an effective amount of compounds of the formula

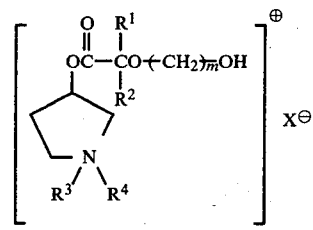
I wherein $R^1$ and $R^2$ are the same or different and are phenyl optionally substituted with a substituent selected from the group $C_1$ to $C_6$ alkyl, $C_1$ to $C_6$ alkoxy and halo; or; monovalent heterocyclic radical of aromatic character containing, in addition to a heteroatom which is oxygen, nitrogen or sulfur, 4 or 5 carbon atoms in the ring; $R^3$ and $R^4$ are the same or different and are $C_1$ to $C_6$ alkyl; m is the integer 2 through 5; and X is an anion which effectively forms a pharmaceutically acceptable, non-toxic salt.

* * * * *